(12) United States Patent
Sanders et al.

(10) Patent No.: US 6,979,390 B2
(45) Date of Patent: Dec. 27, 2005

(54) METHOD AND APPARATUS FOR SEPARATING BIOLOGICAL MOLECULES

(75) Inventors: Giles Hugo William Sanders, Maidenhead (GB); John Hassard, London (GB); Stuart Hassard, Richmond (GB); Dimitrios Sideris, Richmond (GB)

(73) Assignee: Deltadot Limited, London (GB)

( * ) Notice: Subject to any disclaimer, the term of this patent is extended or adjusted under 35 U.S.C. 154(b) by 226 days.

(21) Appl. No.: 10/450,498

(22) PCT Filed: Oct. 23, 2001

(86) PCT No.: PCT/GB01/04696

§ 371 (c)(1),
(2), (4) Date: Nov. 17, 2003

(87) PCT Pub. No.: WO02/48177

PCT Pub. Date: Jun. 20, 2002

(65) Prior Publication Data

US 2004/0100268 A1 May 27, 2004

(30) Foreign Application Priority Data

Dec. 15, 2000 (GB) .................................... 0030708

(51) Int. Cl.⁷ .................... G01N 27/447; G01N 27/453
(52) U.S. Cl. ...................... 204/459; 204/610; 204/601; 204/451
(58) Field of Search ................. 204/451–455, 204/601–605, 459, 610

(56) References Cited

U.S. PATENT DOCUMENTS 6,676,819 B1 * 1/2004 Liu et al. ..................... 204/451
6,764,817 B1 * 7/2004 Schneider ........................ 435/4

FOREIGN PATENT DOCUMENTS

| WO | WO 96/35946 | 11/1996 |
|---|---|---|
| WO | WO 00/17631 | 3/2000 |
| WO | WO 02/12876 A2 | 2/2002 |
| WO | WO 02/12877 A2 | 2/2002 |
| WO | WO 02/13122 A2 | 2/2002 |

OTHER PUBLICATIONS

International Search Report for International Application No. PCT/GB01/04696 filed Oct. 23, 2001, mailed Feb. 13, 2002.

* cited by examiner

*Primary Examiner*—Alex Noguerola
(74) *Attorney, Agent, or Firm*—Wallenstein Wagner & Rockey, Ltd.

(57) ABSTRACT

A system for separating biological molecules includes a chip (10) on which there is an electrophoresis separation microchannel (16). At the start of the channel there is an isoelectric focusing section (14) containing a gel having a pH gradient. Molecules to be separated are placed in the focusing section (14) and move to an equilibrium position under the influence of an electric field. The electrophoretic state of the molecules is then changed, and a high voltage potential applied across the entire length of the focusing and separation sections. The molecules migrate under the influence of the electric field from the focusing section into the separation section where their position and velocity are tracked. From a knowledge of position and velocity, a user can determine both charge/mass ratio and isoelectric equilibrium point for each molecule. The gels can be replicated in the chip to allow parallel analysis, and hence comparisons, to take place.

28 Claims, 4 Drawing Sheets

METHOD AND APPARATUS FOR SEPARATING BIOLOGICAL MOLECULES

This Application is the U.S. National Stage of International Application No. PCT/GB01/04696, with an international filing date of 23 Oct. 2001, now pending, claiming priority from Great Britain Application No. GB00/30708.2, with a filing date of 15 Dec. 2000, now pending, and herein incorporated by reference.

TECHNICAL FIELD

The present apparatus relates to a method and apparatus for separating biological molecules. It finds particular, although not exclusive, application in the separation, for identification purposes, of proteins and like molecules.

BACKGROUND OF THE INVENTION

In conventional protein mapping, exemplified by the SDS-page technique, differing properties of the proteins are used to separate them out into a two-dimensional map. Typically, proteins acquired from a sample are first separated out according to their isoelectric equilibrium points, by depositing them on a pH graded strip-gel. Under a moderate electric field, the proteins are allowed to establish their isolectric equilibrium points within that gel. The strip-gel is then placed onto the edge of a conventional two-dimensional electrophoresis separation plate in an SDS-page system. A strong orthogonal electric field then causes the proteins to migrate in the second dimension, across the plate, according to their charge/mass ratio. The SDS (sodium dodecasulfate) changes the electrophoretic state of the molecules so that, when they are on the plate, they move at a speed proportional to their charge/mass ratio. The smaller proteins move faster than the larger ones (their mobility in the constant field being higher) and, eventually, one ends up with a two-dimensional or orthogonal separation of the proteins across the surface of the plate. At the end of the separation procedure, each protein appears as a separate spot on the gel.

To undertake further tests on the separated proteins, the individual spots may be dug out of the gel, or otherwise extracted, and investigated for example in a mass spectrometer.

There are a number of problems with this known technique, including the slowness of the separation, the clumsiness of the rather ad hoc procedures required, the fact that many manipulations are needed with the consequent susceptibility to systematic errors, and the impossibility of doing parallel analyses for comparison.

It is an object of the present invention at least to alleviate these difficulties of the prior art.

SUMMARY OF THE INVENTION

According to a first aspect of the invention there is provided a method of separating biological molecules, comprising:
(a) applying a first electric field to the molecules to cause them to migrate, along a common linear focusing channel, towards their respective isoelectric equilibrium points, to produce a linear isoelectric separation;
(b) changing the electrophoretic state of the molecules; and
(c) applying a second electric field to the isoelectric separation to cause the molecules to migrate and separate along a common linear separation channel.

According to a second aspect, there is provided apparatus for separating biological molecules, comprising:
(a) a linear focusing channel arranged, when a first electric field is applied along the length of the channel, to cause molecules to migrate towards their respective isoelectric equilibrium points to produce a linear isoelectric separation; and
(b) a common linear separation channel along which the molecules migrate when a second electric field is applied to the isoelectric separation.

With the apparatus and method of the present invention, precise and rapid separations may be carried out essentially in one dimension, without requiring the use of two-dimensional gels as in the prior art. This brings a number of advantages, specifically the possibility of improved and simpler pattern recognition, which can be carried out in real time. That itself allows the possibility, in certain embodiments, selectively to collect proteins or other molecules of interest using a fast high voltage switch, for example applied at a bifurcation or polyfurcation in the separation channel. That allows the easy isolation of a given molecule after having recognised it in software.

The use of an essentially one-dimensional separation system, allowing in some embodiments for the simultaneous measurement of both molecular charge/mass ratio and also isoelectric equilibrium point, allows the possibility of using multiple channels in parallel. This provides the capability of carrying out comparative studies in real time, something which has been difficult or impossible with previous techniques.

The first or isoelectric focusing channel may be embodied in a number of ways. It is essentially a linear channel, which may be straight or curved. Possible embodiments include an elongate length or strip of isoelectric focusing material, for example a gel having a predefined pH gradient. Alternatively, the channel may be defined by a channel, groove or tunnel which has been cut, grown or otherwise formed in a chip. The channel will typically include some isoelectric focusing gel having a predefined pH gradient.

The separation channel is once again, essentially a linear channel which may either be curved or straight. It may be defined for example by a capillary or by a channel, groove or tunnel cut, grown or otherwise formed in a chip. Typically, the channel will contain an electrophoresis gel, normally with no pH gradient.

The invention extends to any compatible combination of different features described or shown in connection with different embodiments. It further extends to any compatible combination of features or concepts set out in the introduction or referred to in any of the claims.

BRIEF DESCRIPTION OF THE DRAWINGS

The present invention may be carried into practice in a number of ways and several specific embodiments will now be described, by way of example, with reference to the accompanying drawings, in which.

DETAILED DESCRIPTION OF THE PREFERRED EMBODIMENT

Figure 1:
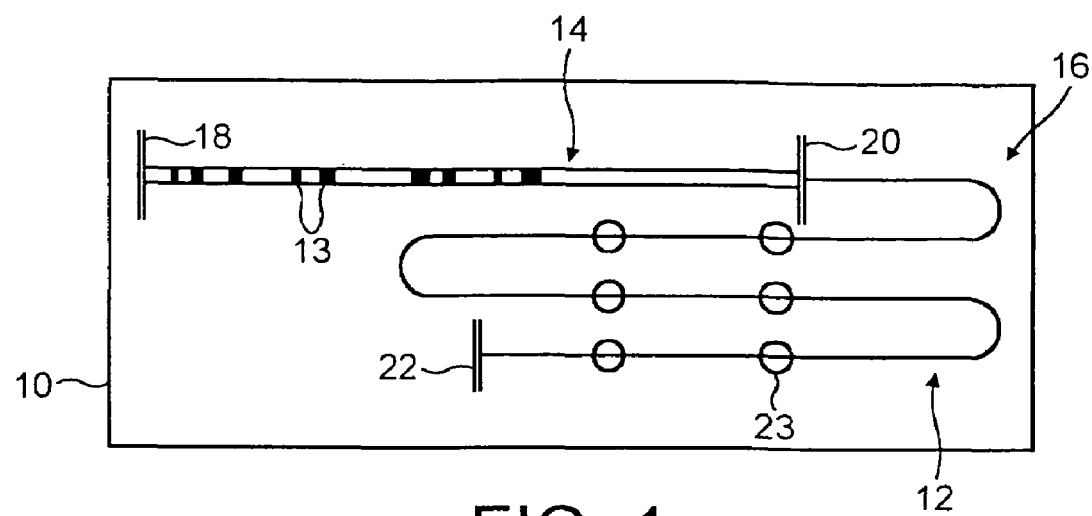
FIG. 1 shows a first embodiment of the invention.

Turning first to FIG. 1, there is shown a first embodiment of the invention in which, as with all of the embodiments, molecular separation is achieved essentially in one-dimension, rather than the two of the prior art. The device shown comprises a chip 10 of PDMS (polydimethylsiloxane), silicon, sapphire, diamond or some combination of these. On or within the chip is a micro-channel generally indicated at 12. The channel may have a width of anything from a fraction of a micrometre to hundreds of micrometres, and a depth from a fraction of a micrometre to thousands of micrometres. In the preferred embodiment, however, the micro-channel is about 50 micrometers wide, and about 500 micrometres deep.

The channel is divided up into two parts, namely the focusing section generally indicated at 14 and a separation section generally indicated at 16. The channel 12 contains an electrophoretic gel. This preferably has a uniform isoelectric potential throughout the separation section 16, and a varying isoelectric potential in the focusing section. It is preferable that there is no discontinuity at the boundary between the focusing section and the separation section. For ease of operation, it is preferred that the isoelectric potential gradient within the focusing section 14 is linear, although that is not essential. The relative lengths of the focusing section and the separation section may be chosen according to the separation task at hand.

A sample of protein to be separated is introduced into the end of the focusing section 14, and the molecules are allowed to establish their equilibrium points under the influence of a moderate electric field generated by applying a potential difference between electrodes 18,20 at either end of the focusing section. The moving proteins are imaged (for example followed under the microscope) until they reach their equilibrium points 13. At these points, the molecules are, by definition, electrically neutral with respect to their surroundings.

In order to allow the molecules now to move into the separation section 16, their electrophoretic state must be changed (since otherwise the proteins would not move). This can be achieved by denaturing the proteins (for example by heating or by applying a wash of detergent such as SDS). Typically, detergent will already be present in the separation section 16—to ensure that the molecules remain in their denatured state during the separation phase—so the addition of a similar detergent to the focusing section 14 does not cause any particular difficulty. Alternatively, or in addition the pH gradient within the focusing section may be destroyed. In another embodiment (not shown) there may be a single body of gel, part of which has a pH gradient and part of which does not, the latter part acting as the separation channel.

Once electrophoretic mobility has been restored to the focused proteins, a high voltage is supplied between the electrode 18 at the start of the focusing section and a further electrode 22 at the end of the separation section. This causes the proteins to move along the channel with a velocity proportional to their charge/mass ratio.

Conventional systems may be used to image the resultant separated proteins, once the electrophoresis has been allowed to continue for sufficient time. The resultant bands may, for example, be photographed and measured either automatically or manually. Alternatively, fixed detectors 23 along the length of the separation section may track the bands as they move along, allowing the bands to be identified in real time. Preferably, the bands are imaged using the label-free intrinsic imaging techniques described in our patent application WO-A-9635945. This case is incorporated by reference.

At the end of the separation phase, the proteins have been separated/identified both by molecular weight (determined by the velocity of movement during the separation phase, or the position a particular band has reached after a known time) and also in isoelectric potential (based on each molecule's "starting position" for the separation phase, that is its isoelectric equilibrium point within the focusing section 14). Both the charge/mass ratio, and the isoelectric point, may be extracted from measurements taken on the molecular bands as they pass down the separation section: see for example our patent applications PCT/GB011/03281, PCT/GB01/03275, PCT/GB01/03286 and WO-A-9635946, all of which are incorporated by reference.

FIG. 1 shows an "in series" transfer from the focusing section to the separation section, in other words an arrangement in which the focusing channel is end-to-end contiguous with the separation channel, so that molecules leaving the end of the focusing channel move straight into the start of the separation channel.

The array of sensors 23 detects the moving bands of molecules, in real time, as they pass along the separation section. Since the position of each of these sensors is known, and the time taken for each band to arrive at a respective sensor is also known, the velocity of each band can be determined. Since the velocity is proportional to the charge/mass ratio, a knowledge of the velocity enables the ratio and hence the molecular weight of the molecules to be determined. By taking timing measurements for each of the bands at a variety of different sensors, one can then "vertex back" as described in our PCT application PCT/GB01/03286 to determine the start point for each band, in other words each band's isoelectric focusing point within the focusing section 14. Data capture and analysis are carried out in real time by an associated computer system (not shown).

Figure 2:
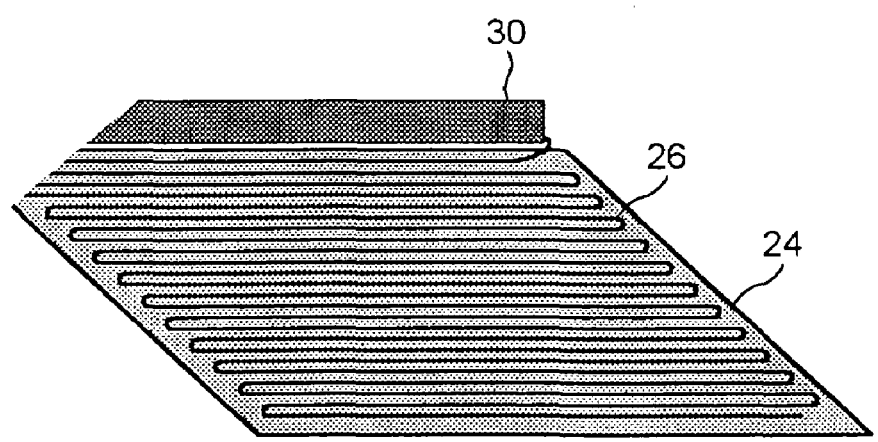
FIG. 2 shows a second embodiment.

FIG. 2 shows an alternative embodiment, in which the focused molecules are transferred, sideways, from the focusing section to the start of the separation section.

FIG. 2 shows a chip 24 having a raster-pattern separation channel 26. The start of the separation channel defines a channel loading portion 28 which is arranged to have positioned next to it a commercially-available isoelectric focusing strip 30 having a pre-defined pH gradient along its length. In use, molecules to be separated are placed on the strip, and are allowed to migrate to their equilibrium positions under the influence of an electric field (not shown). Once equilibrium has been achieved, the strip is removed from the field and placed on the chip adjacent to the loading section 28. The focused molecules are then transferred sideways onto the loading section, and electrophoresis can then take place in the normal way along the separation section 26.

Figure 3:
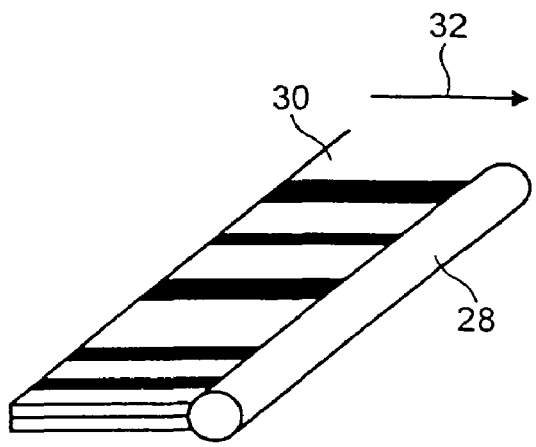
FIG. 3 illustrates the way in which proteins may be moved from the focusing channel to the separation channel.

The transfer of the molecules from the focusing strip to the loading section can be achieved in a variety of ways. As is best seen in FIG. 3, the molecules can be moved sideways by electrophoresis, simply by applying a short pulse field in the direction of the arrow 32. Alternatively, the molecules can be transferred across by washing and/or blotting.

As before, in order to allow movement of the molecules within the separation section, the electrophoretic state of the molecules has to be changed. This could be done as described above. Alternatively, if sufficient detergent (such as SDS) is present within the loading portion 28, that may in itself be enough to denature the proteins. Other techniques may also be employed to achieve this result.

In exactly the same way as the first embodiment, the proteins are imaged as they separate along the separation section 26. The protein molecular weights are established by measuring the velocity at a multitude of points, and are reconstructed by one or a combination of the techniques mentioned above. The PCT/GB01/03286 algorithm is then used to establish where within the loading section 28 the protein started from. We thus get the protein velocity, which is a measure of its molecular weight, and also the starting point, which is a measure of the isoelectric potential in which the protein originally found equilibrium.

Figure 4:
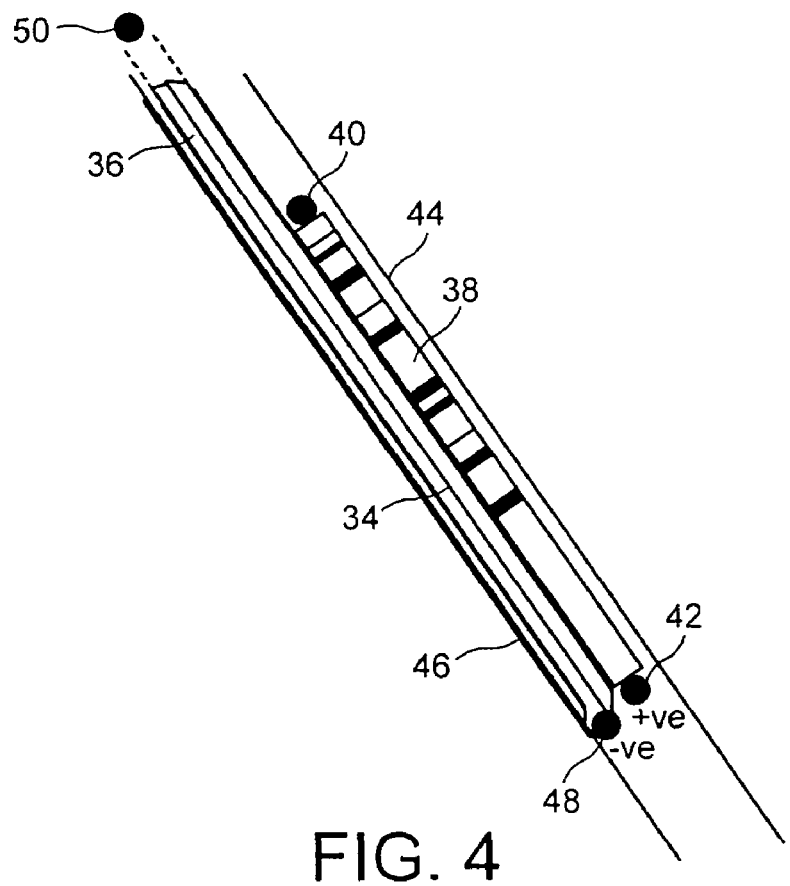
FIG. 4 shows the transfer mechanism in a single chip system.

A rather similar sideways transfer mechanism, but this time embodied on a single chip, is shown schematically in FIG. 4. Here, a loading section 34 of a separation channel 36 lies adjacent to a short focusing channel 38 which contains a gel having a pH which varies along its length. A sample of molecules to be separated is first loaded into the focusing channel 38 and the molecules allowed to move to their equilibrium positions under the influence of an electric field generated by a potential difference applied between electrodes 40,42. Once equilibrium has been reached, the molecules are moved sideways into the separation channel by a pulse voltage applied to lateral electrodes 44,46. A separation voltage is then applied between separation electrodes 48,50, causing the molecules to migrate down the separation channel 36 towards the electrode 50. As before, there may be a need for an intermediate step to change the electrophoretic state of the molecules to ensure that they move along the separation channel.

In alternative embodiments, it may be convenient to replicate the separation channels numerous times on a single chip, so that multiple separations may be carried out in parallel. This provides much greater throughput, and also allows direct comparisons of two or many samples. For example, one sample could be that of a suspect cancer patient, the other from a benchmark sample. Or one could be with a drug-moderated sample, another the benchmark. Similarly, the relative changes induced by changes in a given pharmacogenitic regime can be studied. In a typical 40 mm×40 mm chip, there could be for example 128 such channels, with the channel width for the electrophoretic channel (separation section) and that of the isoelectric channel (focusing section) both being 50 micrometres across.

Figure 5A:
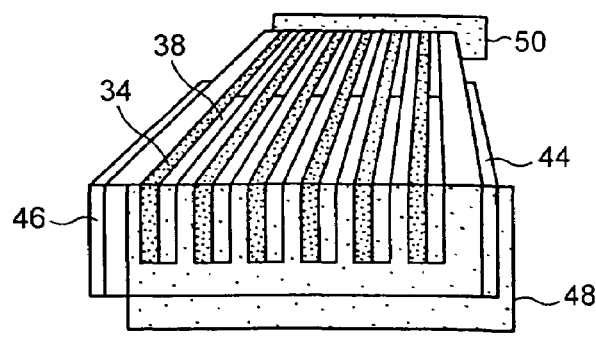
FIG. 5(a) shows the chip topology in a multi-channel embodiment.

An exemplary specific embodiment of this type, in which both the focusing section and the separation section are contained on a single chip, is shown in FIG. 5(a). It will, however, be understood that both the FIG. 1 and the FIG. 2 embodiments could also be manufactured with multiple parallel microchannels.

In FIG. 5, identical reference numerals are used to those that were used in FIG. 4. Accordingly, the speckled areas 48,50 represent the electrophoresis electrodes, with numerals 44,46 the lateral electrodes (the electrodes 40,42 used to create the isoelectric equilibrium are not shown). Reference 38 shows the focusing microchannel, with its graded isoelectric gel, and 34 the adjacent separation microchannel with its electrophoresis gel. Alternatively, there may be a single microchannel in the chip for each one with part of the microchannel being taken up with gel having a pH gradient and an adjacent part with gel having no pH gradient, the latter of course forming the separation channel. The molecules are then simply moved sideways from one part of the gel to the other.

Figure 5B:
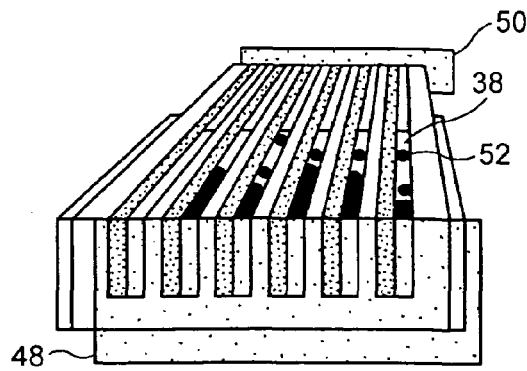
FIG. 5(b) shows the isoelectric separation phase.

As shown in FIG. 5(b), proteins 52 are first inserted into the focusing microchannel 38, and allowed to reach equilibrium while a potential difference is applied between the electrodes 40,42 (FIG. 4).

Figure 5C:
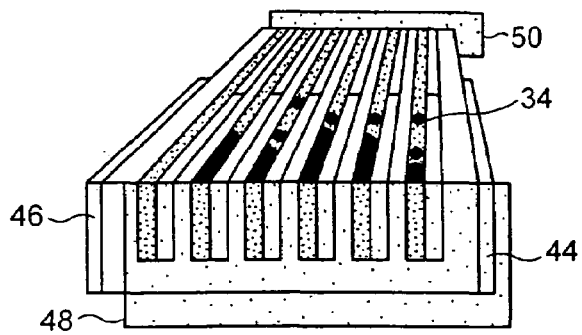
FIG. 5(c) shows the electrophoretic insertion phase.

Next, as shown in FIG. 5(c), as the protein bands reach equilibrium, the voltage is applied across the lateral electrodes 44,46 to move the proteins sideways into the separation microchannel 34.

Figure 5D:
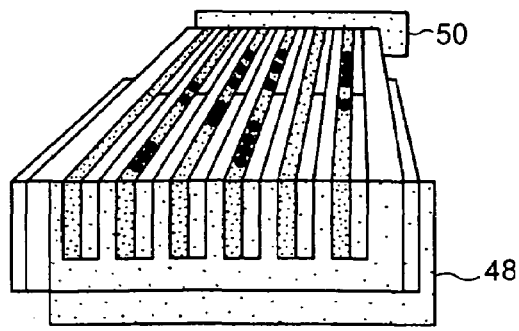
FIG. 5(d) shows the electrophoretic separation phase.

Finally, as shown in FIG. 5(d) a voltage is applied across the electrophoresis electrodes, causing the proteins-to migrate along the separation channels, where they are tracked and imaged (not shown).

In either the single channel or in the multi-channel embodiments, pattern-recognition may be carried out in real time, with selected molecules being automatically collected at the end of the separation channel according to the results of the analysis. This may preferably be achieved by providing a bifurcated end to one or all of the separation channels, as shown in FIG. 7, with selected samples being collected by means of a high voltage switch which is automatically actuated according to the results of the analysis procedure being carried out in real time.

Figure 7:
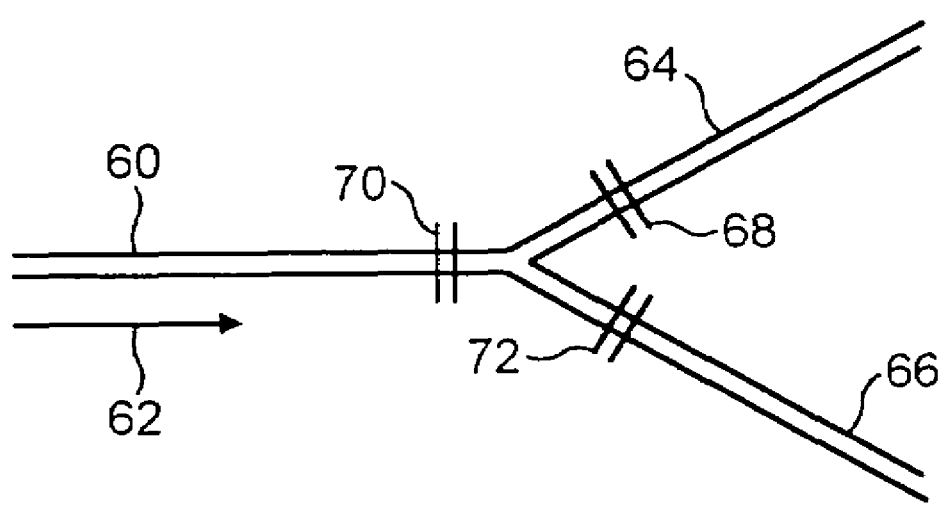
FIG. 7 shows the preferred molecular collection system.

The preferred collection mechanism is shown schematically in FIG. 7. The end portion 60 of the separation microchannel is bifurcated, and includes a first path 64 and a second path 66. When a particular molecular band that is to be collected reaches the bifurcation, travelling in the direction of the arrow 62, a high collection voltage is applied between electrodes 70 and 72, to cause the molecules to pass down into the channel 66. Once the required sample has been collected, the collection voltage is switched across electrodes 68 and 70, thereby causing all the following molecules to pass down into the channel 64. A given sample protein of interest can then be isolated in real time after automatic software recognition.

Figure 6:
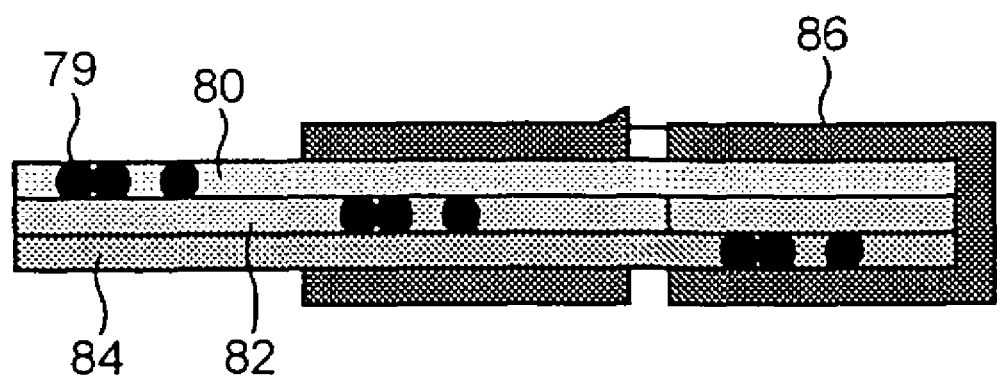
FIG. 6 shows yet another embodiment, making use of three channels.

The general concepts discussed above can be generalised to the use of more than one separation channel. For example, as shown in FIG. 6, molecules 79 for separation are initially placed into a first channel 80, and allowed to separate. Once separation in that channel is complete, the molecules are moved across into a second channel 82, with the molecules then moving in that channel. Finally, the molecules are moved across into a third channel 84 where the process is repeated. The position and/or velocity of the molecules within the channels 80,82,84 may be detected in real-time by detectors 86. More channels could of course be envisaged. The mechanisms by which the molecules move within the individual channels will typically be different, to allow independent study of various aspects of the molecular configuration or structure. The channels may differ in a variety of ways, according to the separations required or the molecular aspects being studied. The differing channel characteristics could include electric fields, magnetic fields, pH gradients, chemical concentration gradients, temperature gradients, density gradients and so on. This allows various differing properties of the molecules to be used, to allow even greater selectivity and resolution.

What is claimed is:

1. A method of separating biological molecules, comprising:

(a) applying a first electric field to the molecules to cause them to migrate, along a common linear focusing channel, towards their respective isoelectric equilibrium points, to produce a linear isoelectric separation;

(b) changing the electrophoretic state of the molecules; and (c) applying a second electric field to the isoelectric separation to cause the molecules to migrate and separate along a common linear separation channel.

2. A method as claimed in claim 1 in which the focusing channel is adjacent to at least an initial portion of the separation channel.

3. A method as claimed in claim 1 in which the focusing channel is end-to-end contiguous with the separation channel, so that molecules leaving the end of the focusing channel move into the start of the separation channel.

4. A method as claimed in claim 1 in which the electrophoretic state of the molecules is changed by denaturing.

5. A method as claimed in claim 1 in which the electrophoretic state of the molecules is changed by exposing them to a detergent.

6. A method as claimed in claim 1 in which the electrophoretic state of the molecules is changed by heating.

7. A method as claimed in claim 1 further including either measuring or determining the velocity of the molecules as they migrate along the separation channel.

8. A method as claimed in claim 1 further including determining, from the movement of the molecules within the separation channel, their respective charge/mass ratios and isoelectric equilibrium points.

9. A method as claimed in claim 1 further including analysing the movement of the molecules along the separation channel and automatically collecting a sample of molecules of interest in dependence upon a result of the analysis.

10. A method as claimed in claim 1 in which the molecules are proteins.

11. An apparatus for separating biological molecules, comprising:

(a) a linear focusing channel arranged, when a first electric field is applied along a length of the channel, to cause molecules to migrate towards their respective isoelectric equilibrium points to produce a linear isoelectric separation; and (b) a common linear separation channel along which the molecules migrate when a second electric field is applied to the isoelectric separation.

12. An apparatus as claimed in claim 11 in which the focusing channel is disposed adjacent to at least an initial portion of the separation channel.

13. An apparatus as claimed in claim 12 further including transfer means for transferring the molecules sideways from the focusing channel into the separation channel.

14. An apparatus as claimed in claim 13 in which the transfer means comprises electrodes for creating an electric field.

15. An apparatus as claimed in claim 13 in which the transfer means comprises blotter means.

16. An apparatus as claimed in claim 12 further including a further separation channel adjacent to the said separation channel.

17. An apparatus as claimed in claim 12 in which the focusing channel and the separation channel are provided on a common gel.

18. An apparatus as claimed in claim 11 in which the focusing channel is end-to-end contiguous with the separation channel so that molecules leaving the end of the focusing focusing channel move into the start of the separation channel.

19. An apparatus as claimed in claim 11 in which the apparatus includes a chip, with the separation channel being defined by a channel on the chip.

20. An apparatus as claimed in claim 19 in which the focusing channel is also defined by a channel on the chip.

21. An apparatus as claimed in claim 19 in which the focusing channel is defined by an isoelectric focusing strip.

22. An apparatus as claimed in claim 11 further including means for either measuring or determining the velocity of the molecules as they migrate along the separation channel.

23. An apparatus as claimed in claim 11 further including means for determining, from the movement of the molecules within the separation channel, their respective charge/mass ratios and isoelectric equilibrium points.

24. An apparatus as claimed in claim 11 further including means for analysing the movement of molecules along the separation channel and means for automatically collecting a sample of molecules of interest.

25. An apparatus as claimed in claim 11 further including a plurality of adjacent linear separation channels.

26. An apparatus as claimed in claim 25 including a corresponding plurality of adjacent linear focusing channels.

27. An apparatus as claimed in claim 11 including a plurality of focusing channels and a corresponding plurality of adjacent separation channels all contained on a single chip.

28. An apparatus as claimed in claim 27 further including first and second lateral electrodes for generating an electric field to simultaneously transfer the molecules in each focusing channel sideways into a corresponding adjacent separation channel.

* * * * *